US010782266B1

(12) United States Patent
Crall et al.

(10) Patent No.: US 10,782,266 B1
(45) Date of Patent: Sep. 22, 2020

(54) NON-DESTRUCTIVE EVALUATION OF INTERNAL DAMAGE IN FIBER REINFORCED COMPOSITE MATERIALS BY DELIVERY OF A TWO-PART MAGNETIC NANOPARTICLE CHEMISTRY

(71) Applicant: The University of Tulsa, Tulsa, OK (US)

(72) Inventors: Matthew Crall, Little Rock, AR (US); Samuel Laney, Tulsa, OK (US); Michael Keller, Tulsa, OK (US)

(73) Assignee: The University of Tulsa, Tulsa, OK (US)

( * ) Notice: Subject to any disclaimer, the term of this patent is extended or adjusted under 35 U.S.C. 154(b) by 196 days.

(21) Appl. No.: 15/799,462

(22) Filed: Oct. 31, 2017

Related U.S. Application Data

(60) Provisional application No. 62/415,125, filed on Oct. 31, 2016.

(51) Int. Cl.
| | |
|---|---|
| *G01N 27/82* | (2006.01) |
| *B29C 70/88* | (2006.01) |
| *G01N 21/88* | (2006.01) |
| *G01N 25/72* | (2006.01) |
| *B29K 309/08* | (2006.01) |

(52) U.S. Cl.
CPC ............. *G01N 27/82* (2013.01); *B29C 70/88* (2013.01); *G01N 21/8803* (2013.01);
(Continued)

(58) Field of Classification Search
CPC ................. C08K 9/10; C08K 2201/01; C08K 2003/2265; G01N 27/84; G01N 2203/0062; G01N 33/54326; G01N 27/82; G01N 27/825; G01N 33/54236; G01N 21/8803; G01N 25/72; H01F 1/44; H01F 1/447; H01F 41/16; H01F 41/44; H01F 41/447; H05K 2201/083; H05K 1/0269;
(Continued)

(56) References Cited

U.S. PATENT DOCUMENTS

| | | | | |
|---|---|---|---|---|
| 2007/0087198 | A1* | 4/2007 | Dry ......................... | C04B 28/02 428/408 |
| 2015/0226579 | A1* | 8/2015 | Nino ...................... | G01N 19/08 73/774 |

OTHER PUBLICATIONS

Naebe et al., Crack Damage in Polymers and Composites: A Review, Jan. 2016.*

(Continued)

*Primary Examiner* — Camie S Thompson
(74) *Attorney, Agent, or Firm* — Head, Johnson, Kachigian & Wilkinson, PC

(57) ABSTRACT

A method of making a fiber reinforced composite material having a two-part liquid solution forming magnetic nanoparticles. The method includes the steps of preparing a fiber reinforced composite having dispersed fibers and a polymer matrix and having a plurality of vascular channels therethrough. A first liquid solution is incorporated in at least one of the vascular channels and a second liquid solution is incorporated in at least one other of the vascular channels. When the liquid solutions are joined together because of damage or cracking to the composite, the liquids form a ferrous magnetic material. Non-destructive evaluation of internal damage to the fiber reinforced composite material may be accomplished by magnetic field disturbance detection, thermal detection, or visual detection.

16 Claims, 2 Drawing Sheets

(52) U.S. Cl.
CPC .......... *G01N 25/72* (2013.01); *B29K 2309/08* (2013.01); *B29K 2995/0008* (2013.01)

(58) Field of Classification Search
CPC ............ H05K 2203/161; A61K 9/5094; B29C 73/22; B29C 70/88; B29K 2105/06; B29K 2995/0008; B32B 2307/762; Y10T 428/2902; Y10T 428/2913; Y10T 428/2924; Y10T 428/2971; Y10T 428/249994; B01J 13/18
USPC ........... 252/301.19, 62.51 R, 62.52, 56, 513; 257/E21.502; 324/214, 216; 73/799; 427/8, 96.2; 428/297.4, 313.3, 320.2, 428/258, 370, 396, 188
See application file for complete search history.

(56) References Cited

OTHER PUBLICATIONS

Mimi Hetti, et al.; Magnetite Core-Shell Nanoparticles in Nondestructive Flaw Detection of Polymeric Materials; ACS Publications; Sep. 27, 2016; DOI: 10.1021/acsami.6b09934; ACS Appl. Mater Interfaces 2016, 8, 28208-28215.

Matthew D. Crall, et al.; Self-Healing Polymeric Material Synthesized by Guiding Magnetic Microcapsules; pending U.S. Appl. No. 15/612,256, filed Jun. 2, 2017.

* cited by examiner

NON-DESTRUCTIVE EVALUATION OF INTERNAL DAMAGE IN FIBER REINFORCED COMPOSITE MATERIALS BY DELIVERY OF A TWO-PART MAGNETIC NANOPARTICLE CHEMISTRY

CROSS-REFERENCE TO RELATED APPLICATIONS

This application claims priority to and the benefit of U.S. Provisional Patent Application Ser. No. 62/415,125, filed Oct. 31, 2016, which is herein incorporated in its entirety by reference.

FEDERALLY SPONSORED RESEARCH OR DEVELOPMENT

This invention was developed with the assistance of a National Science Foundation grant (CMMI 1351760). The U.S. Government may have rights in this invention.

BACKGROUND OF THE INVENTION

Field of the Invention

The present invention is directed to a fiber reinforced composite material and a method of making a fiber reinforced composite material having a two-part liquid solution. When the fiber reinforced composite material is subject to damage or cracking, the two liquid solutions join together to form a ferrous magnetic material. Non-destructive evaluation of damage or cracking in the fiber reinforced composite material is accomplished by sensing the ferrous magnetic material within the composite material.

Description of the Related Art

It is possible to test materials or components by placing them in conditions until they reach failure mode. For example, materials or components may be put under stress until cracking or until breakage. The load or stress limit is thereby determined.

Non-destructive testing or non-destructive evaluation may also be used to evaluate the properties of the material or component without causing damage. Because the component or material is not permanently altered after being inspected, it is a valuable process.

There are currently very few methods available for detecting damage in structural composites. Those that do exist, such as ultrasonic c-scanning, are expensive and/or impractical for use in routinely detecting varieties of damage, such as cracking and delamination. As such, most composite structures are over-designed to allow for the presence of damage that may not be detected during routine inspections. This results in structures that are larger, heavier, and more expensive than necessary.

The present invention allows for the construction of composite materials, such as laminates, that respond well to at least three different types of damage detection (visual, magnetic field disturbance, and thermal detection) that were not previously available for fiber reinforced composites. These inspection methods are much more easily and cheaply implemented than existing methods. The ability to incorporate, embed, or inject solutions into a structural component and thereby easily detect hidden internal damage or cracking is both novel and useful. This allows for the creation of composites that are more high-performance, since damage can be easily detected and dealt with, rather than over-designing components to be strong enough to handle hidden, undetectable damage that may or may not be present. For example, this is especially valuable in industries like aerospace where weight of materials is of primary concern.

Accordingly, it is a principal object and purpose of the present invention to provide a method of non-destructive testing or evaluation of internal damage or cracking in fiber reinforced composite material.

It is a further object and purpose of the present invention to provide a method of making a fiber reinforced composite material having a two-part liquid solution which forms magnetic nanoparticles when the two solutions are brought together.

It is a further object and purpose of the present invention to provide a fiber reinforced composite material having a two-part liquid solution embedded in vascular channels in the composite material.

It is a further object and purpose of the present invention to provide a fiber reinforced composite material having a two-part liquid solution wherein non-destructive evaluation of internal damage or cracking may be determined by magnetic field disturbance detection, thermal detection, or visual detection.

SUMMARY OF THE INVENTION

The present invention is directed to a method of making fiber reinforced composite material having a two-part liquid solution incorporated, embedded, or injected therein.

In one preferred embodiment, the method includes preparing a fiber reinforced composite having dispersed fibers in a polymer matrix and having a plurality of vascular channels therethrough. A first liquid solution in at least one of the vascular channels is incorporated in the fiber reinforced composite. At least one other of the vascular channels includes a second liquid solution incorporated in the fiber reinforced composite material. Neither the first liquid solution nor the second liquid solution is magnetic. In one non-limiting example, at least one of the liquid solutions may be a ferrous salt solution.

When the composite material is damaged or cracked, the first liquid solution and the second liquid solution are brought together to form a ferrous magnetic material.

In one non-limiting embodiment, each of the first liquid solution and the second liquid solution are microencapsulated into capsules. Damage or cracking of the composite ruptures the capsules, causing the two liquid solutions to join together and form a ferrous magnetic material.

The present invention includes a method of non-destructive evaluation of internal damage or cracking in fiber reinforced composite material. The ferrous magnetic material formed from the joinder of the first liquid solution and the second liquid solution is sensed in a number of ways. Non-destructive evaluation includes visual detection, magnetic field disturbance detection, or thermal detection.

The present invention is also directed to a fiber reinforced composite material having a two-part liquid solution forming magnetic nanoparticles. The material is composed of a fiber reinforced composite having dispersed fibers therein in a polymer matrix and having a plurality of vascular channels therethrough. A first liquid solution is contained in at least one of the vascular channels and a second liquid solution is contained in at least one other of the vascular channels. Neither the first liquid solution nor the second solution is magnetic. When the first liquid solution and the second liquid solution are brought together, they form a ferrous magnetic material.

Each of the first and second liquid solutions may be microencapsulated into capsules. Damage or cracking of the composite material ruptures the capsules.

The present invention may further be directed to a method of non-destructive evaluation of internal damage or cracking in fiber reinforced material. The method includes sensing ferrous magnetic material within a fiber reinforced composite material wherein the ferrous magnetic material is formed from a first liquid solution joined with a second liquid solution. The ferrous magnetic material may be sensed via magnetic field disturbance detection, thermal detection, or visual detection.

DETAILED DESCRIPTION OF THE INVENTION

The embodiments discussed herein are merely illustrative of specific manners in which to make and use the invention and are not to be interpreted as limiting the scope.

While the invention has been described with a certain degree of particularity, it is to be noted that many modifications may be made in the details of the invention's construction and the arrangement of its components without departing from the scope of this disclosure. It is understood that the invention is not limited to the embodiments set forth herein for purposes of exemplification.

Figure 1:
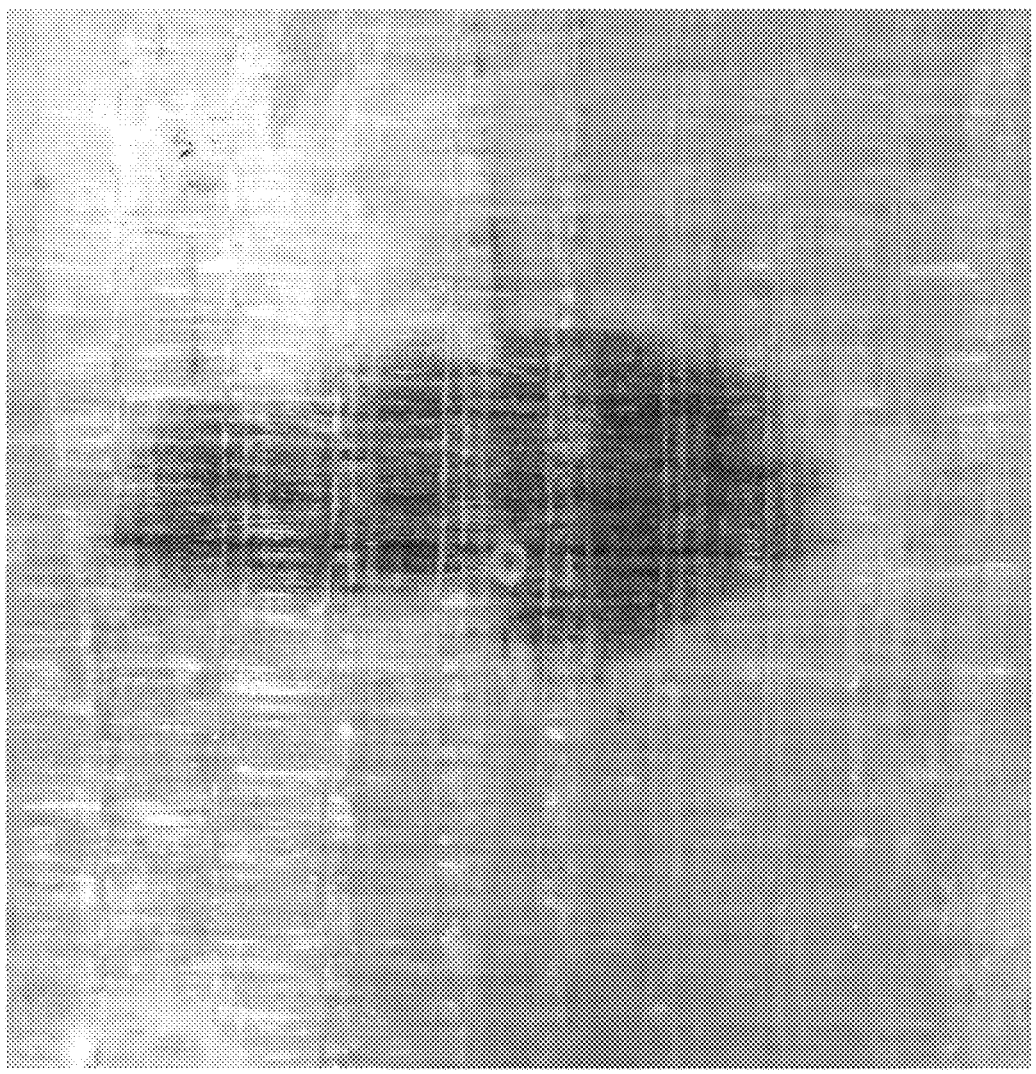
FIG. 1 is a photograph of an example of a fiber reinforced composite material having a two-part solution wherein internal damage or cracking to the composite material has formed magnetic nanoparticles which are visible in accordance with non-destructive evaluation of internal damage of the present invention.

Referring to the drawings in detail, FIG. 1 illustrates a photo of an example of a fiber reinforced composite material. In the present embodiment, a fiberglass reinforced composite material sheet is shown, although other types of composite materials are possible. The composite material has dispersed fibers and a polymer matrix. The polymer matrix is nonferromagnetic.

In one preferred embodiment, the fiber reinforced composite material includes a plurality of vascular channels through the composite material. The vascular channels may be formed in a variety of ways. In one method, the vascular channels are formed by incorporating thin wires in the dispersed fibers and polymer matrix prior to curing and thereafter removing the wires after curing to form the vascular channels. In another method, the channels are formed between layers of the fiber reinforced composite during fabrication of the material. Other methods of forming or creating vascular channels are possible within the spirit and scope of the invention.

The vascular channels may have widths anywhere from a few millimeters to a few microns. In one non-limiting example, the channels may be approximately 10 microns wide.

Strategies may be employed to minimize any impact on the structural integrity of the composite material.

A first liquid solution is incorporated, embedded, or injected in at least one or more of the vascular channels. In addition, a second liquid solution is incorporated, embedded, or injected in at least one other of the vascular channels. Each of the liquid solutions is incorporated within the fiber reinforced composite material, but each is separate and distinct from the other so that the solutions never react with each other.

Neither the first liquid solution nor the second liquid solution is magnetic. Instead, in one embodiment, the solutions are various salts. In one non-limiting example, one of the liquid solutions may be a ferrous salt solution. When the fiber reinforced composite material having the liquid solutions therein is damaged or is cracked, the first liquid solution joins with the second liquid solution. A chemical reaction takes place between the two solutions, thereby forming a ferrous magnetic material.

The two liquid solutions interact in the damaged or cracked region forming highly magnetic nanoparticles where the damage or cracking has occurred. These nanoparticles can be visually seen in some laminates, such as shown in FIG. 1. The damage or cracking can alternately be detected using magnetic field disturbance detection sensors or, alternatively, by thermal detection.

Figure 2:
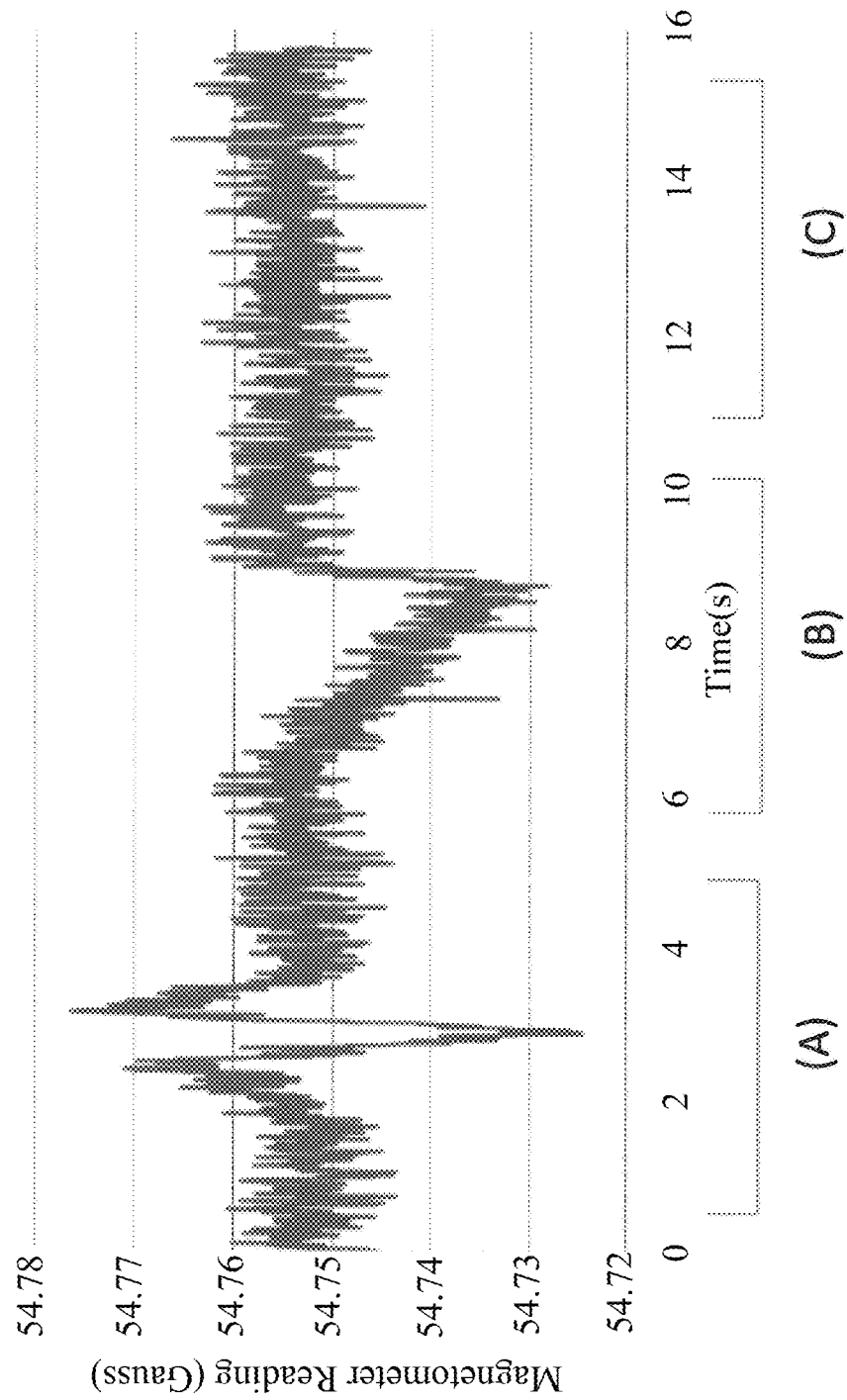
FIG. 2 is a graph or chart illustrating the results of magnetic field disturbance detection during different time periods in accordance with the present invention.

FIG. 2 illustrates a chart or graph of results of magnetic field disturbance detection during different tests on the fiber reinforced composite material shown in FIG. 1. Magnetic field disturbance detection detects a change in the magnetic field.

The time component is shown on the X axis and a magnetometer reading is shown on the Y axis. The time portion A shows the results of magnetic readings while a magnetic field disturbance sensor was swept over the damaged region of the composite material. Readings from the time period B show the sensor brought directly over the top of the damaged region. Finally, the time period C shows readings of the sensor passed over undamaged regions. The magnetometer readings are stable in this time period. Accordingly, it will be seen that magnetic field disturbance detection indicates where damage or cracking has occurred in the composite material.

Similar detection may be performed via thermal detection.

Whereas, the invention has been described in relation to the drawings attached hereto, it should be understood that other and further modifications, apart from those shown or suggested herein, may be made within the scope of this invention.

What is claimed is:

1. A method of making a fiber reinforced composite material having a two-part liquid solution forming magnetic nanoparticles, which method comprises:
   preparing a fiber reinforced composite having dispersed fibers in a polymer matrix and having a plurality of vascular channels therethrough;
   incorporating a first liquid solution in at least one of said vascular channels and incorporating a second liquid solution in at least one other of said vascular channels; and
   wherein neither said first liquid solution nor said second liquid solution is magnetic and wherein said first and said second solutions together form a ferrous magnetic material when joined together.

2. The method as set forth in claim 1 including the additional steps of forming said vascular channels by incorporating wires in said dispersed fibers and polymer matrix prior to curing and thereafter removing said wires after curing.

3. The method as set forth in claim 1 including the additional steps of forming said vascular channels by fabricating said fiber reinforced composite materials from layers with channels therebetween.

4. The method as set forth in claim 1 wherein each of said first liquid solution and said second liquid solution are microencapsulated into capsules and wherein damage or cracking ruptures the capsules.

5. The method as set forth in claim 1 wherein at least one of said liquid solutions is a ferrous salt solution.

6. A fiber reinforced composite material having a two-part liquid solution forming magnetic nanoparticles, which material comprises:
   a fiber reinforced composite having dispersed fibers in a polymer matrix and having a plurality of vascular channels therethrough;
   a first liquid solution in at least one of said vascular channels and a second liquid solution in at least one other of said vascular channels; and
   wherein neither said first liquid solution nor said second liquid solution is magnetic and wherein said first and said second liquid solutions together form a ferrous magnetic material when joined together.

7. A fiber reinforced composite material as set forth in claim 6 wherein each of said first and said second liquid solutions are microencapsulated into capsules and damage or cracking ruptures the capsules.

8. A fiber reinforced composite material as set forth in claim 6 wherein at least one of said liquid solutions is a ferrous salt solution.

9. A method of non-destructive evaluation of internal damage or cracking in fiber reinforced composite material, which method comprises:
   sensing ferrous magnetic material within a fiber reinforced composite material wherein said ferrous magnetic material is formed from a first liquid solution joined with a second liquid solution; and
   wherein neither said first liquid solution nor said second liquid solution is magnetic and wherein said first and said second liquid solutions together form a ferrous magnetic material when joined together.

10. A method of non-destructive evaluation as set forth in claim 9 including a plurality of vascular channels in said fiber reinforced composite material.

11. A method of non-destructive evaluation as set forth in claim 10 wherein said first liquid solution is incorporated in at least one of said vascular channels and wherein said second liquid solution is incorporated in at least one other of said vascular channels.

12. A method of non-destructive evaluation as set forth in claim 9 wherein said step of sensing ferrous magnetic material is accomplished via magnetic field disturbance detection.

13. A method of non-destructive evaluation as set forth in claim 9 wherein said step of sensing ferrous magnetic material is accomplished via thermal detection.

14. A method of non-destructive evaluation as set forth in claim 9 wherein said step of sensing ferrous magnetic material is accomplished via visual detection.

15. A method of making a fiber reinforced composite material having a two-part liquid solution forming magnetic nanoparticles, which method comprises:
   preparing a fiber reinforced composite having dispersed fibers in a polymer matrix and having a plurality of vascular channels therethrough;
   incorporating a first liquid solution in at least one of said vascular channels and incorporating a second liquid solution in at least one other of said vascular channels; and
   including the additional steps of forming said vascular channels by incorporating wires in said dispersed fibers and polymer matrix prior to curing and thereafter removing said wires after curing.

16. A method of making a fiber reinforced composite material having a two-part liquid solution forming magnetic nanoparticles, which method comprises:
   preparing a fiber reinforced composite having dispersed fibers in a polymer matrix and having a plurality of vascular channels therethrough;
   incorporating a first liquid solution in at least one of said vascular channels and incorporating a second liquid solution in at least one other of said vascular channels; and
   including the additional steps of forming said vascular channels by fabricating said fiber reinforced composite materials from layers with channels therebetween.

* * * * *